(12) United States Patent
Kandori et al.

(10) Patent No.: US 11,172,849 B2
(45) Date of Patent: Nov. 16, 2021

(54) MOVEMENT FUNCTION ASSESSMENT SYSTEM AND MOVEMENT FUNCTION MEASUREMENT APPARATUS

(71) Applicant: MAXELL, LTD., Kyoto (JP)

(72) Inventors: Akihiko Kandori, Tokyo (JP); Yuko Sano, Tokyo (JP); Kanako Esaki, Tokyo (JP); Yuhua Zhang, Tokyo (JP)

(73) Assignee: MAXELL, LTD., Kyoto (JP)

( * ) Notice: Subject to any disclaimer, the term of this patent is extended or adjusted under 35 U.S.C. 154(b) by 22 days.

(21) Appl. No.: 15/506,484

(22) PCT Filed: Jun. 12, 2015

(86) PCT No.: PCT/JP2015/067040
§ 371 (c)(1),
(2) Date: Feb. 24, 2017

(87) PCT Pub. No.: WO2016/031349
PCT Pub. Date: Mar. 3, 2016

(65) Prior Publication Data
US 2017/0251957 A1 Sep. 7, 2017

(30) Foreign Application Priority Data
Aug. 28, 2014 (JP) .............................. JP2014-174276

(51) Int. Cl.
*A61B 5/11* (2006.01)
*A61B 5/00* (2006.01)
*A61B 5/06* (2006.01)

(52) U.S. Cl.
CPC .......... *A61B 5/1126* (2013.01); *A61B 5/0002* (2013.01); *A61B 5/062* (2013.01);
(Continued)

(58) Field of Classification Search
CPC ... A61B 5/1126; A61B 5/0002; A61B 5/1125; A61B 5/1127; A61B 5/1114; A61B 5/11;
(Continued)

(56) References Cited

U.S. PATENT DOCUMENTS

2004/0034299 A1* 2/2004 Kandori ............. A61B 5/04007
600/409
2004/0158167 A1* 8/2004 Smith .................... A61B 5/053
600/547
(Continued)

FOREIGN PATENT DOCUMENTS

CN 101080198 A 11/2007
JP H10-154293 A 6/1998
(Continued)

OTHER PUBLICATIONS

International Search Report for WO 2016/031349 A1, dated Sep. 8, 2015.
(Continued)

*Primary Examiner* — Matthew Kremer
*Assistant Examiner* — Avery M Foley
(74) *Attorney, Agent, or Firm* — Volpe Koenig (57) ABSTRACT

The present invention addresses the problem of limiting power consumption and radio wave interference when assessing the movements of multiple sites of a living body. The present invention is a movement function assessment system provided with: a movement function measurement apparatus for calculating movement data on the basis of the relative distances of pairs of transmission coils and reception coils attached to movable portions of a living body; and an assessment apparatus for assessing the movement function of the living body on the basis of the movement data received from the movement function measurement apparatus. A control unit of the movement function measurement
(Continued)

apparatus performs the switching of the multiple transmission coils by a switching unit (1) and the switching of the multiple reception coils by a switching unit (2) so that the paired transmission coils and reception coils are operated sequentially.

10 Claims, 11 Drawing Sheets

(52) U.S. Cl.
CPC ........... *A61B 5/1114* (2013.01); *A61B 5/1123* (2013.01); *A61B 5/4082* (2013.01); *A61B 5/6826* (2013.01); *A61B 5/7225* (2013.01)

(58) Field of Classification Search
CPC ....... A61B 5/062; A61B 5/061; A61B 5/1123; A61B 5/4082; A61B 5/6826; A61B 5/7225
See application file for complete search history.

(56) References Cited

U.S. PATENT DOCUMENTS

| | | | |
|---|---|---|---|
| 2005/0065422 A1* | 3/2005 | Kandori | A61B 5/1101 600/407 |
| 2007/0185398 A1 | 8/2007 | Kimura et al. | |
| 2007/0244388 A1* | 10/2007 | Sato | A61B 1/00147 600/424 |
| 2007/0272599 A1 | 11/2007 | Miyashita et al. | |
| 2009/0192418 A1 | 7/2009 | Miyashita et al. | |
| 2011/0095758 A1* | 4/2011 | Walsh | A61B 5/7203 324/307 |
| 2012/0130203 A1* | 5/2012 | Stergiou | A61B 5/0002 600/301 |
| 2014/0228905 A1* | 8/2014 | Bolea | A61F 5/56 607/42 |
| 2015/0234017 A1* | 8/2015 | Yamamoto | G01R 33/063 324/244 |

FOREIGN PATENT DOCUMENTS

| | | |
|---|---|---|
| JP | 2006-288831 A | 10/2006 |
| JP | 3841075 A | 11/2006 |
| JP | 2007-301003 A | 11/2007 |

OTHER PUBLICATIONS

First Chinese Office Action dated Mar. 20, 2019 for the Chinese Patent Application No. 201580046355.7.
Second Chinese Office Action dated Aug. 2, 2019 for the Chinese Patent Application No. 201580046355.7.
Final Chinese Office Action dated Nov. 29, 2019 for the Chinese Patent Application No. 201580046355.7.
Chinese Office Action dated Aug. 14, 2020 for Chinese Patent Application No. 201580046355.7.
XTAT386, Section 13.3 Multi-channel analog switch (Jan. 31, 1995) (with English concise explanation of relevance for Section 13.3).

* cited by examiner

MOVEMENT FUNCTION ASSESSMENT SYSTEM AND MOVEMENT FUNCTION MEASUREMENT APPARATUS

TECHNICAL FIELD

The present invention relates to a technique of assessing a movement function of a biological object.

BACKGROUND ART

Recent in Japan, the number of patients suffering from cranial nerve disorders (hereinafter, referred to as "cranial nerve disorders patients") such as dementia, Parkinson's disease, and stroke has been increasing rapidly. For example, Parkinson's disease is a cranial nerve disorder including 4 main symptoms of tremor (shaking), muscle rigidity (one of conditions that muscle tensions are high), postural reflex disorder (poor posture restoration), and bradykinesia (slowness of movement). In addition, regarding dementia, it is said that there are as many as two million dementia patients in Japan, and the memory loss, disorientation, and learning disability are caused by dementia so that their daily lives are obstructed seriously. Even in dementia, at a terminal stage at latest, movement disorders such as walking with a few rapid, short shuffling steps and a forward-flexed posture are found in the patients, and they finally become bedridden.

Human movements are realized in such a way that movement commands from a brain pass as electric signals through nervous system, and corresponding to the electric signals muscles contract. However, in case of cranial nerve disorders patients, the movement commands from the brain cannot pass normally as the electric signals to the nervous system, so that abnormalities are generated in bodily condition and action.

The rapid increase of the cranial nerve disorders patients causes not only an increase of medical care expense but also a great social loss because those patients have incapacities for work. Accordingly, in order to solve the social problem caused by such cranial nerve disorders patients, it is required to determine whether a subject has the cranial nerve disorders or not, if so, to determine a progress of the cranial nerve disorders with a certain accuracy or higher.

However, it is difficult to determine whether the subject has the cranial nerve disorders or not and the progress thereof by a blood test and imaging findings of MRI (Magnetic Resonance Imaging) or the like. This is because differences between cranial nerve disorders patients and able-bodied persons are not always clear. Accordingly, it is often the case that whether the subject has the cranial nerve disorders or not and the progress are determined subjectively by experience and ability of a doctor. With such a background, in order to assess degradation of the movement functions and a tuning disorder caused by Parkinson's disease, for example, a finger movements test for monitoring movements of finger has been conducted.

As a method of monitoring such finger movements, the methods using, for example, an electric switch, a metal loop, a keyboard, and a 3-dimentional camera and the like have been invented. However, those methods are not so simple as to be sufficiently popular.

Thus, the present applicant proposes a biological assessment apparatus capable of detecting using a magnetic sensor a movement of portions of the biological object (for example, a movement of repeatedly opening/closing the two fingers of one hand (a thumb and an index finger) (hereinafter, referred to as "finger tapping movement") of two fingers) (see Japanese Patent No. 3841075). According to Japanese Patent No. 3841075, it is possible to determine whether the subject is the cranial nerve disorder patient or the able-bodied person with high accuracy by analyzing information obtained from the finger tapping movement and recognizing the movements of the two fingers of the subject.

Meanwhile, as a method of electronically detecting a displacement of a vehicle in its width direction, a technique of switching connections between a plurality of detection coils one by one using an exciting power supply having the same frequency to obtain a detection signal of one of the detection coils in time division is disclosed (see Japanese Unexamined Patent Application Publication No. H10-154293). In the technology of Japanese Patent Application No. H10-154293, an output signal of a crystal oscillator is amplified to be supplied to exciting coils through a change-over switch. It is believed that this technology would provide an electronic vehicle position detection system which may electronically detect maker information mainly on a present travelling position of the vehicle and the displacement of the vehicle in its width direction.

SUMMARY OF INVENTION

Technical Problem

However, with a configuration (providing each of the hands with a measurement circuit) in the technology of Japanese Patent No. 3841075, in order to measure the movements of both of the hands at the same time, it is necessary to arrange two oscillators having different frequencies corresponding to each of the hands and also arrange two detection circuits corresponding to each of the hands so that circuit scale may be expanded and power consumption may also become large. Consequently, when the technology of Japanese Patent No. 3841075 is applied into a portable device driven by battery, measurement for a short time can only be achieved, thus it is not practical. Further, Japanese Patent No. 3841075 uses a technology by which crosstalk (interference) in detecting the movements of left and right hands can be prevented by using the different frequencies, however, the crosstalk (interference) can be caused when both of the hands become very close to each other.

Furthermore, since a technology of Japanese Patent Application No. H10-154293 provides a configuration to obtain position information of the markers arranged at intervals from several meters to dozens of meters for solving the problem of detecting electronically the displacement of the vehicle in the width direction, temporal concurrency and continuity at a plurality of measurement points are not required. Thus, it is not possible to detect a continuous waveform at a plurality of points almost at the same time. In addition, since the a plurality of points to detect the position of the vehicle are several meters to dozens of meters away from each other not to cause the crosstalk (interference) between each of the measurement points, a configuration to prevent the crosstalk and noise mixing has not been considered. Since there is also little restriction on power consumption of a device mounted on the vehicle, no device has been applied to suppress power consumption.

Accordingly, the present invention addresses the problem of suppressing power consumption and radio wave interference when assessing the movements of a plurality of sites of the biological object.

Solution to Problem

In order to solve the foregoing problem, the present invention provides a movement function assessment system, comprising: a movement function measurement apparatus configured to calculate movement data based on a relative distance between a pair of a oscillation coil and a detection coil attached to movable portions of a biological object; and an assessment apparatus configured to assess the movement function of the biological object based on the movement data received from the movement function measurement apparatus, wherein
the movement function measurement apparatus includes: an alternating current generating unit configured to generate an alternating current of a predetermined frequency; a plurality of oscillation coils; a first switching unit connected with the alternating current generating unit and the plurality of oscillation coils located on each side of the first switching unit, the first switching unit being configured to switch connections between the alternating current generating unit and the plurality of oscillation coils to connect the alternating current generating unit with each of the plurality of oscillation coils one by one so as to flow the alternating current generated by the alternating current generating unit through the each of the plurality of oscillation coils sequentially; a plurality of detection coils, each of which is disposed to be paired with one of the plurality of oscillation coils and configured to detect a magnetic field generated by the one of the plurality of oscillation coils to be paired with the plurality of detection coils; a second switching unit connected with the plurality of detection coils: an amplification/filter unit connected with the plurality of detection coils through the second switching unit; a time adjustment/detection unit connected with the amplification/filter unit, the time adjustment/detection unit being configured to perform detection by using reference signals from the alternating current generating unit; and a control unit configured to have the first switching unit and the second switching unit switch the connections between the alternating current generating unit and the plurality of oscillation coils and between the amplification/filter unit and the plurality of detection coils respectively so that the coil pairs become in operation in a predetermined order with each pair of the oscillation coil and the detection coil in operation simultaneously. Other units will be described below.

Advantageous Effects of Invention

Consequently, it is possible to suppress energy consumption and radio wave interference in assessing the movements of a plurality of sites of the biological object.

BRIEF DESCRIPTION OF DRAWINGS

FIG. 2A and FIG. 2B are diagrams showing the oscillation coils and the detection coils attached to both hands for measuring finger tapping movements.

An upper part of FIG. 5 is a diagram showing the magnetic fields received. A lower part of FIG. 5 is a diagram showing the waveforms remained after performing a deletion processing of noise components for the first one cycle.

FIG. 7A and FIG. 7B are diagrams showing the typical waveforms of the finger tapping movements of one hand.

FIG. 10A and FIG. 10B are diagrams showing the distance waveforms obtained by measuring finger tapping movements of both of the hands of the first comparative example (conventional technology).

FIG. 11A, FIG. 11B, and FIG. 11C are diagrams showing the waveforms measured by the second comparative example (conventional technology).

DESCRIPTION OF EMBODIMENTS

Embodiments for carrying out the present invention (hereinafter, referred to as "embodiments") will be explained in detail in detail with reference to the accompanying drawings.

Figure 1:
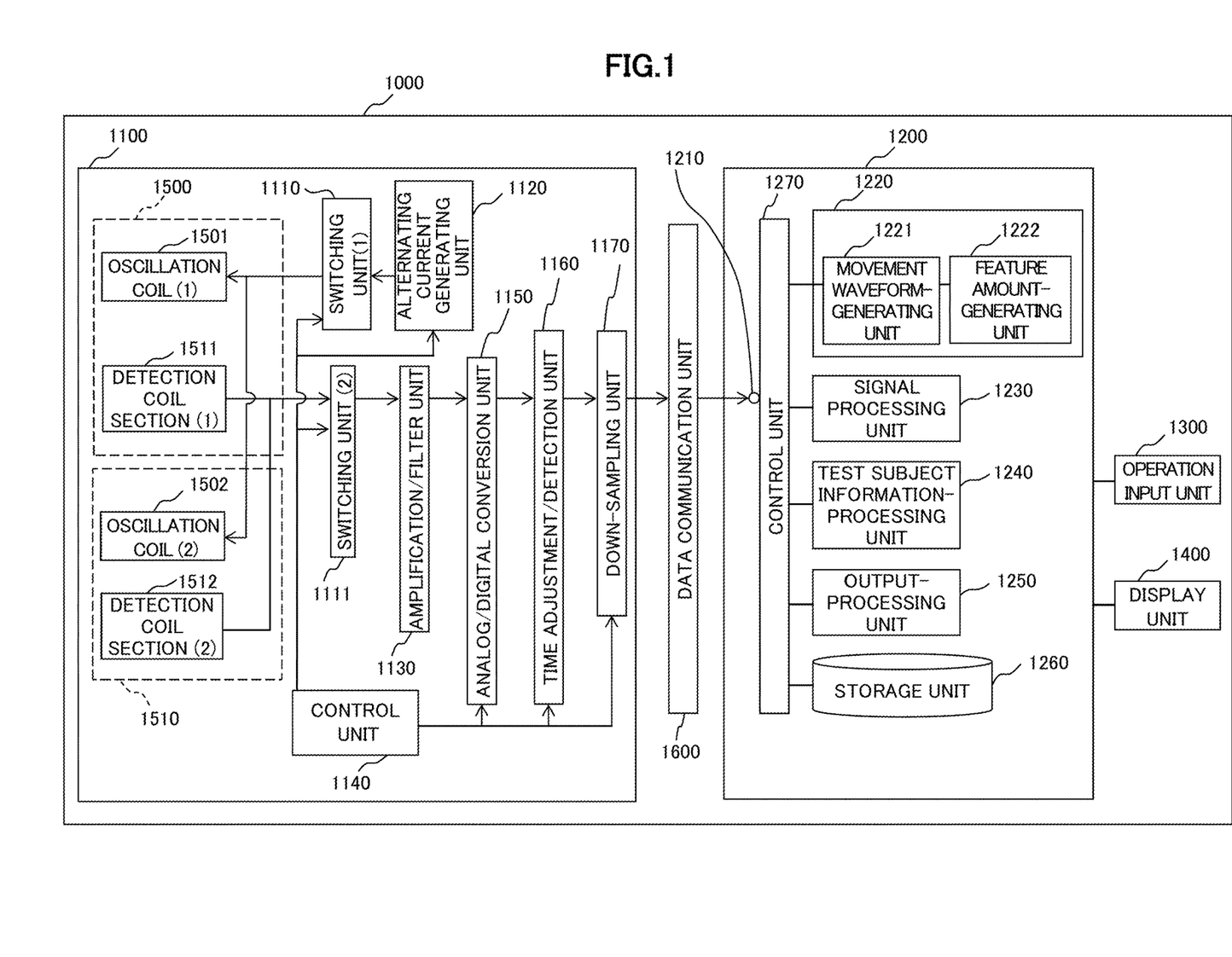
FIG. 1 is a block diagram showing an overall configuration of the movement function assessment system according to this embodiment.

(Overall Configuration) As shown in FIG. 1, a movement function assessment system 1000 according to this embodiment includes a movement function measurement apparatus 1100 for measuring the finger movements of the subject, an assessment apparatus 1200 for recording and analyzing data measured by the movement function measurement apparatus 1100, an operation input unit 1300 for inputting mainly information on the subject, and a display unit 1400 for displaying measurement results and analysis results or the like.

Here, the subject is an object to be measured by the movement function measurement apparatus 1100, and in this embodiment, a person who takes an inspection for checking presence/absence or progress of dementia.

Further, the movement function measurement apparatus 1100 measures the movements of the fingers when the subject is made to perform the finger movement. Here, the finger movement includes the finger tapping movement measured by a magnetic sensor (a movement of repeatedly opening/closing the thumb and the index finger of the one hand as fast as possible and as wide as possible) and all movements of the biological object which can be measured by a distance between two coils. The finger tapping movement will be explained as an example of the finger movements.

(Description of the Movement Function Measurement Apparatus) The movement function measurement apparatus 1100 calculates the movement data based on the relative distance between the oscillation coil and the detection coil attached to the movable portions of the biological object, for example, time-sequentially detects information on the finger movements (hereinafter, also referred to simply as "movement information") of the subject, and obtains the movement information of the subject on at least one of distance, velocity, acceleration, and jerk (which is obtained by performing time differentiation on the acceleration) as time sequential data (waveform data).

The movement function measurement apparatus 1100 includes a sensor 1500 and a sensor 1510, a switching unit (1) 1110 (the first switching unit) and a switching unit (2) 1111 (the second switching unit), an alternating current generating unit 1120, an amplification/filter unit 1130, an analog/digital conversion unit 1150, a time adjustment/detection unit 1160, and a down-sampling unit 1170.

Figure 2A:
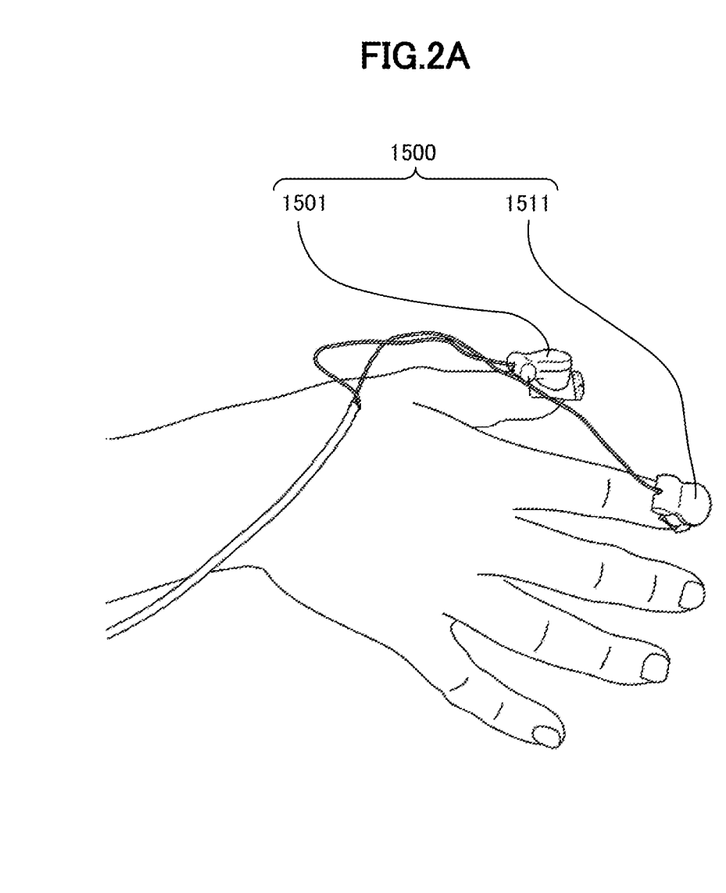
FIG. 2A shows a case where the oscillation coil and the detection coil are attached to a left hand.
Figure 2B:
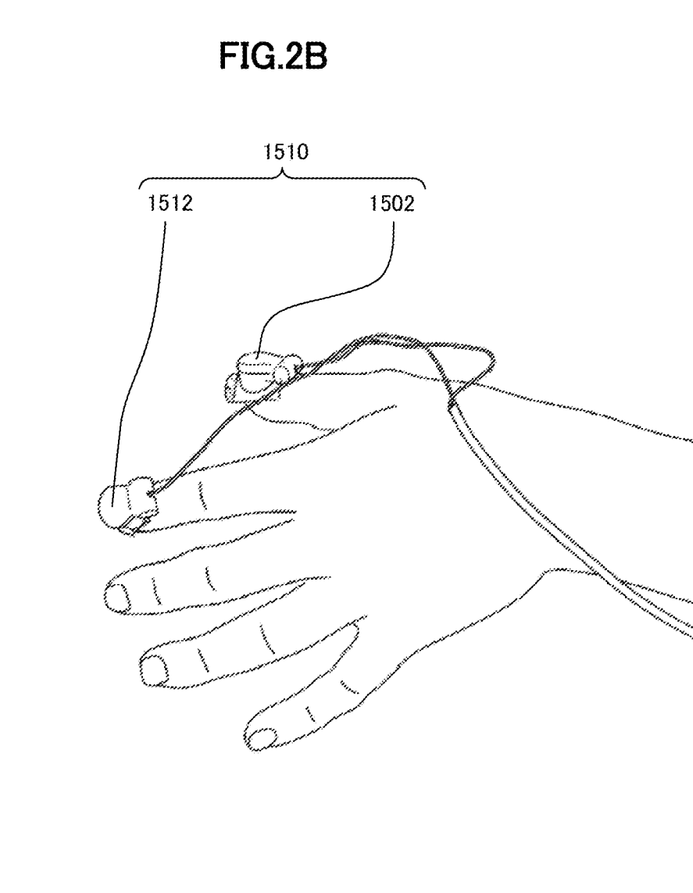
FIG. 2B shows a case where the oscillation coil and the detection coil are attached to a right hand.

(Sensor (Movement Sensor)) As shown in FIG. 2A, the sensor 1500 includes a oscillation coil 1501 for oscillating a magnetic field and a detection coil 1511 for receiving (detecting) the magnetic field. Further, FIG. 2A shows the sensor 1510 is attached to the left hand, and FIG. 2B shows the sensor 1510 is attached to the right hand. Though the following description will be given only of the sensor 1500 for the left hand for simplification, the sensor 1510 for the right hand can be arranged and operated exactly in the same way as the sensor 1500 for the left hand.

As shown in FIG. 2A, the oscillation coil 1501 and the detection coil 1511 are attached to respective nail portions of the thumb and the index finger, for example, by double sided tapes. In addition, by reversing the fingers to be attached, the oscillation coil 1501 and detection coil 1511 may be attached to the respective nail portions of the index finger and thumb.

Further, the description was given by assuming that the portions to which the oscillation coil 1501 and the detection coil 1511 are attached are the respective nail portions of the thumb and the index finger, however, not limited to this, the portions to be attached may be, for example, the finger portions other than the nail portions.

Furthermore, the portions to which the oscillation coil 1501 and the detection coil 1511 are not limited to the thumb and the index finger, for example, the oscillation coil 1501 and the detection coil 1511 maybe attached to be other finger combinations of, for example, the thumb and a little finger. In addition, the portions to be attached are not limited to the nail portions or the fingers of the subject, for example, may include periphery portions such as palms adjacent to the fingers. Accordingly, the portions to which the oscillation coil 1501 and the detection coil 1511 are attached may be either the nail portions, the fingers, or the periphery portions adjacent to the fingers of the subject as long as the finger tapping movements can be detected. In addition, in this embodiment, the description was given by assuming that the attachment to the biological object, however, the oscillation coil and the detection coil are attached to objects other than the biological object so that the relative distance between the oscillation coil and the detection coil can be measured, and that a magnetization degree of metals and movements of magnetized objects can also be measured.

Figure 3:
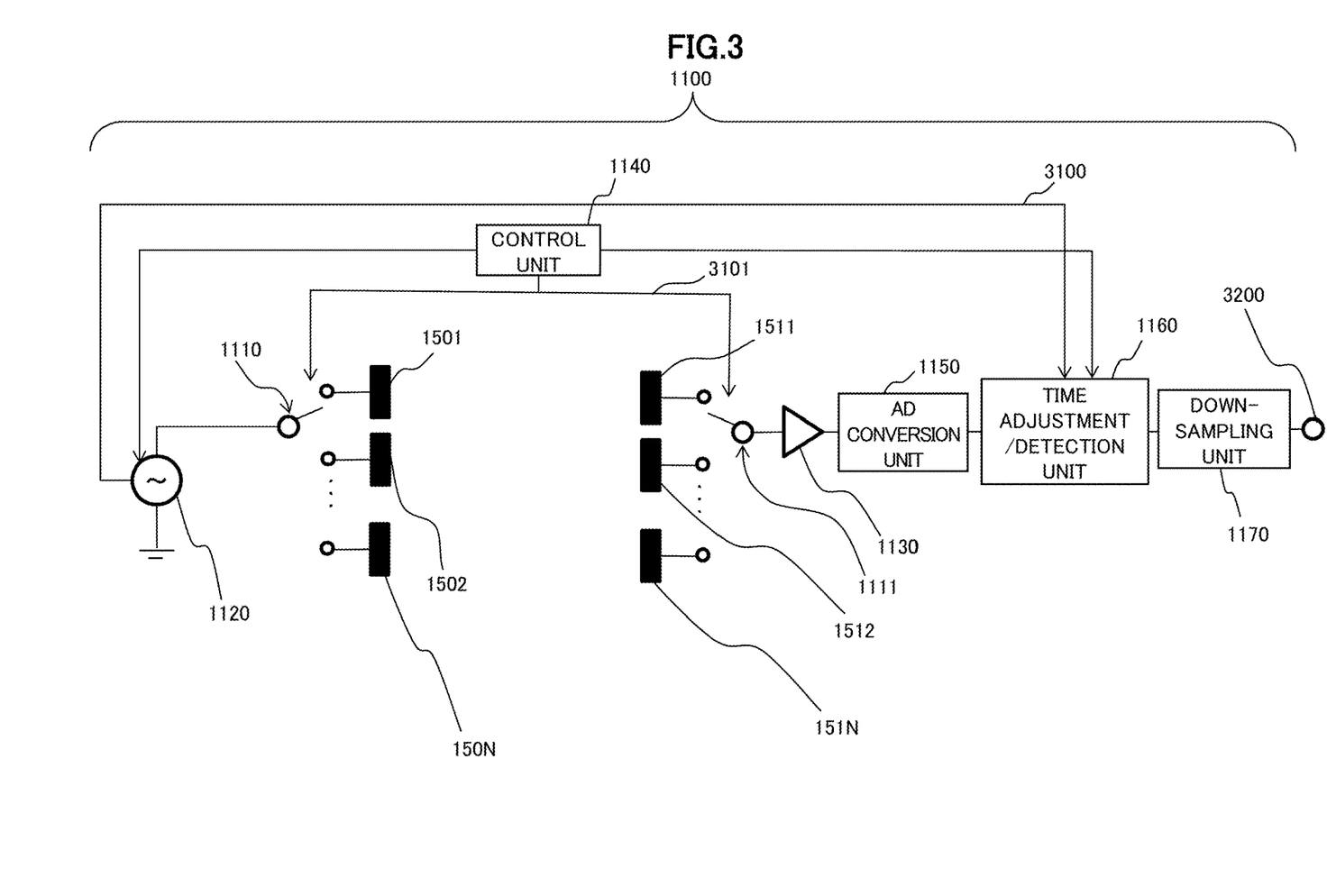
FIG. 3 is a diagram showing an overall configuration of the movement function Measurement apparatus.

(Detailed Description of Movement Function Measurement Apparatus) As shown in FIG. 3, the movement function measurement apparatus 1100 arranges the number N of the oscillation coils from the oscillation coil (1) 1501 to a oscillation coil (N) 150N, and arranges the number N of the detection coils from the detection coil (1) 1511 to a detection coil (N) 151N corresponding to each of the oscillation coils. In other words, a pair to the oscillation coil (1) 1501 is the detection coil (1) 1511, a pair to a oscillation coil (2) 1502 is a detection coil (2) 1512, and a pair to the oscillation coil (N) 150N is the detection coil (N) 151N. Since the movements of the index finger and the thumb are measured in normal finger tapping movements, N equals 2 (namely, in FIG. 3, up to the pair of the oscillation coil (2) 1502 and the detection coil (2) 1512), while the movements of a plurality of (N) sites of the fingers or the like are monitored, it is possible to increase up to the number N of pairs of the oscillation coils and detection coils. In addition, in the description of this embodiment, the plurality of oscillation coils may be collectively referred to simply as "oscillation coils" without signs, and the plurality of detection coils may be collectively referred to simply as "detection coils" without signs.

In this embodiment, a case in which the number of pairs is increased up to N will be described. One alternating current generating unit 1120 (alternating current generating circuit) is connected to the oscillation coils from the oscillation coil (1) 1501 up to the oscillation coil (N) 150N through the switching unit (1) 1110 (selector switch). Further, a switching operation by the switching unit (1) has the alternating current (for example, current of 20 kHz) from the alternating current generating unit 1120 flow sequentially through the each of the oscillation coils so that one of the oscillation coils through which the alternating current has flowed generates an alternating current magnetic field. The alternating current generating unit 1120 generates the alternating current of a predetermined frequency and has a timing to have the current flow controlled by a control unit 1140. More specifically, for saving power, the control unit 1140 controls the alternating current generating unit 1120 so as to perform a oscillating operation only while having the current flow through the number N of the oscillation coils from the oscillation coil (1) 1501 up to the oscillation coil (N) 150N. Further, the signals generated by the alternating current generating unit 1120 are used as reference signals 3100 used in detecting operation by the time adjustment/detection unit 1160.

Further, the control unit 1140 generates a synchronous signal 3101 to control the switching unit (1) 1110 and the switching unit (2) 1111 (selector switch). The synchronous signal 3101 enables the switching unit (1) 1110 and the switching unit (2) to switch simultaneously so that each pair of the oscillation coil and the detection coil becomes in operation simultaneously. In other words, the control unit 1140 have the first switching unit (1) 1110 and the second switching unit (2) 1111 switch the connections between the alternating current generating unit and the plurality of oscillation coils and between the amplification/filter unit and the plurality of detection coils respectively so that the coil pairs become in operation in a predetermined order with each pair of the oscillation coil and the detection coil in operation simultaneously.

The number N of oscillation coils from the oscillation coil (1) 1511 up to the oscillation coil (N) 151N are connected to the amplification/filter unit 1130 (amplification/filter circuit) through the switching unit (2) 1111, the output signal from the amplification/filter unit 1130 are converted to digital signals by the analog/digital (AD) conversion unit 1150, and the digital signals are transmitted to the time adjustment/detection unit 1160. Further, conversion from analog data to digital data by the analog/digital (AD) conversion unit 1150 facilitates subsequent processing (down-sampling and the like). The time adjustment/detection unit 1160 deletes among magnetic field waveforms (noise portions) detected in the detection coils predetermined cycles thereof immediately after the second switching unit (2) 1111 is connected with the each of the plurality of the detection coils (Described in detail in FIG. 4).

Furthermore, the times of the deletion processing in the alternating current magnetic field waveforms of each of the detection coils is controlled accurately by the control unit 1140. After the deletion processing, the time adjustment/detection unit 1160 executes all-wave rectification processing and filter processing (processing mainly by a low-pass filter (LPF)) by using the reference signals 3100. Finally, the digital signals processed in the time adjustment/detection unit 1160 are converted by the down-sampling unit 1170 to rough data (down-sampling) of a sampling frequency (for example, 200 Hz) which is approximately one thousandth (a predetermined ratio) of a sampling frequency (for example, 200 kHz) in the analog/digital (AD) conversion unit 1150. Thereby, it becomes possible to decrease capacity of whole data. Accordingly, the output signal 3200 can be transmitted at high speed as data of the plurality of detection coils even when communication capacity is restricted. In other words, a data communication unit 1600 receives a small amount of data from the down-sampling unit 1170 so as to deliver at one time the movement data on the plurality of detection coils to the assessment apparatus 1200 by radio or cable.

Figure 4:
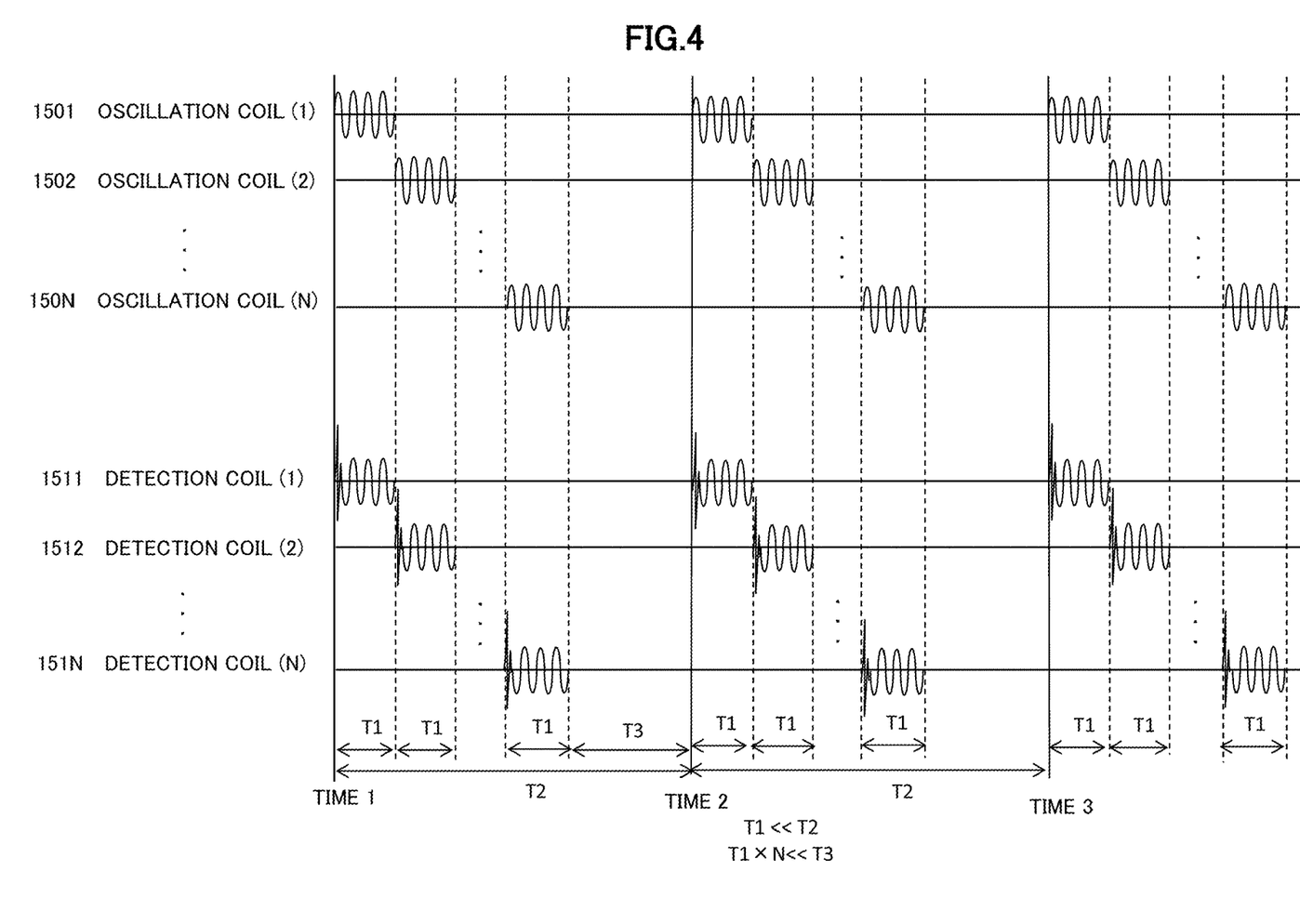
FIG. 4 is a diagram showing the waveforms of the currents flowing through the oscillation coils and the waveforms of the magnetic fields received by the detection coils.

The upper part of FIG. 4 shows the waveforms of currents flowing through the number N of oscillation coils from the oscillation coil (1) 1501 to the oscillation coil (N) 150N, and the lower part of FIG. 4 shows the magnetic field waveforms detected in the number N of the detection coils from the detection coil (1) 1511 to the detection coil (N) 150N. The alternating current is caused to flow through each of the oscillation coils during a time width T1 (for example, 50 μs (200 kHz)) (In FIG. 4, the current waveforms for 4 cycles are shown during the time width T1). Further, the switching unit (1) 1110 (FIG. 3) switches the connections between the alternating current generating unit and the plurality of the oscillation coils and one by one so that the current is caused to flow through each of the oscillation coils up to the Nth oscillation coil (N) 150N at an interval of T1 sequentially.

A time width T2 is, for example, set to 10 ms which is a sampling time of approximately 100 Hz sufficient to measure the maximum frequency 10 Hz possessed, for example, by the finger tapping movements or the like (Namely, a time width between a time 1 and a time 2 and a time width between the time 2 and a time 3 are 10 ms respectively). A time width T3 is obtained by (the time width T2–the time width T1*N), and during the time width T3, control to stop the current flowing from the alternating current generating unit 1120 through the oscillation coils is performed by the control unit 1140 (FIG. 3). Relationships of these time widths are T1<<T2 and T1*N<<T3 (FIG. 4 doesn't represent accurately those relationships for convenience of drawings). Accordingly, during the time width T3 which occupies most of the time width T2, the control to stop the current from the alternating current generating unit 1120 through the oscillation coils enables to suppress current consumption so that power saving can be achieved.

On the other hand, the switching unit (2) 1111 (FIG. 3) switches the connections between the amplification/filter unit and the number N of detection coils from the detection coil (1) 1511 to the detection coil (N) 151N one by one at a timing when the alternating current is caused to flow through one of the oscillation coils to be paired with each of the plurality of the detection coils, and the signals are input into the amplification/filter unit 1130 (FIG. 3). As shown in the lower part of FIG. 4, each of the detection signals (magnetic waveforms) has noise mixed with the first part of the time. The detection noise is generated in such a way that the switching unit (2) 1111 (FIG. 3) switches the connections between the amplification/filter unit and the plurality of the detection coils.

The above problem is caused by measuring without time lags between the signals of the detection coils for the purpose of detecting the signals of all channels (detection coils) almost simultaneously. Supposing measurement of passing vehicles or the like at positions from several meters to dozens of meters away from the passing vehicles, such a problem is not caused because the time lags can be provided between the signals of the detection coils. Further, though both method and a technique of inserting the filter circuit between the detection coils and the amplifier are considered, however, since one cycle is very short, for example, 50 μs in case of a frequency 20 kHz, a delay time due to the filter is longer than the time lags, so that the technique and the method are not practical. Furthermore, for saving power, it is necessary to lengthen the time width T3 by shortening a oscillation time of each of the oscillation coils as much as possible, thus it is necessary to switch each of the channels (detection coils, oscillation coils) without the time lags by shortening T1 of the detection coils and oscillation coils.

Figure 5:
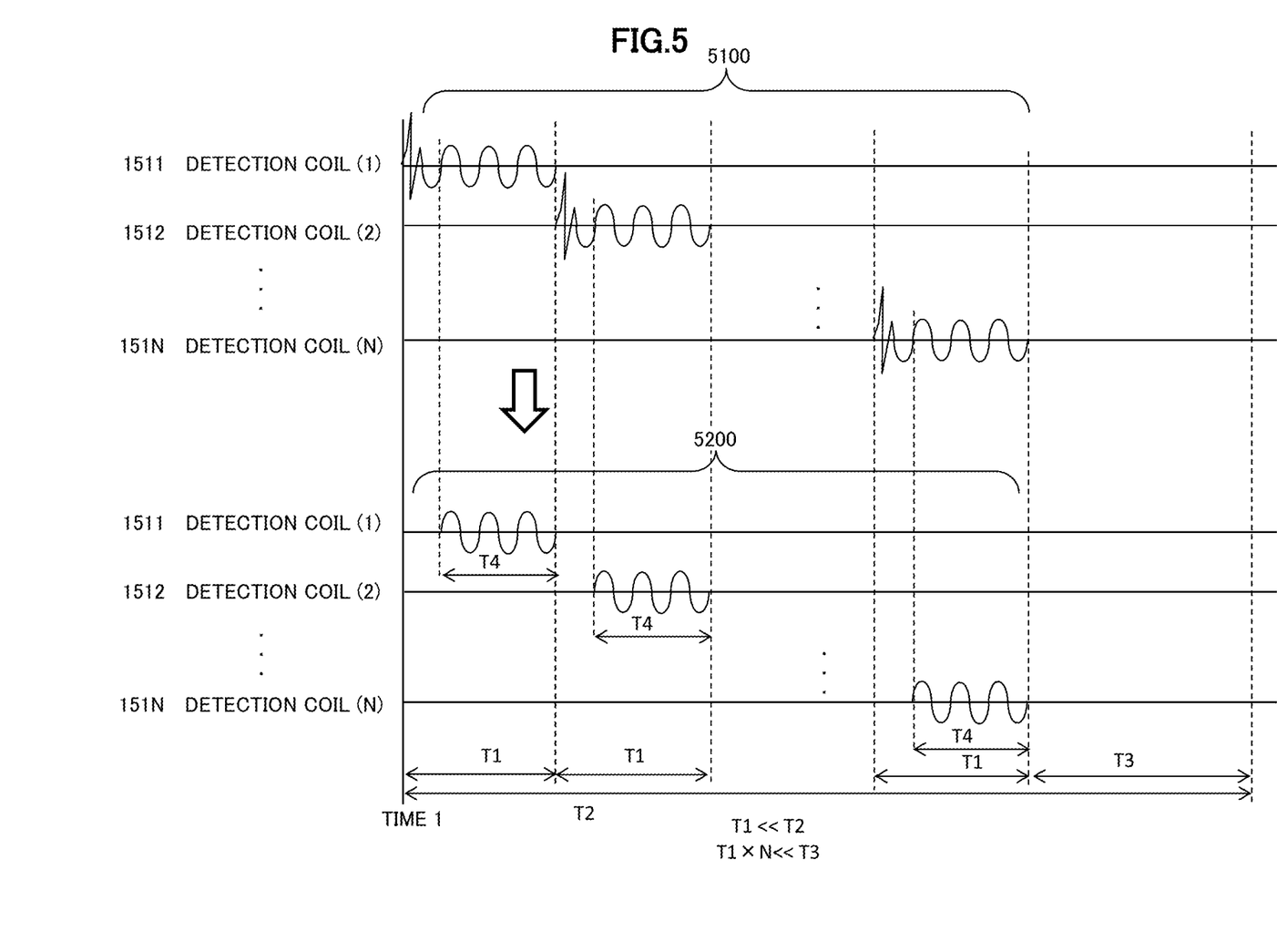

The processing of deleting the noise components which are detected in the detection coils by time adjustment function of the time adjustment/detection unit 1160 will be described in detail with reference to FIG. 5 (see FIG. 1 etc). The magnetic field induced by one of the oscillation coils through which the alternating current generated in the alternating current generating unit 1120 flows are detected in each of the detection coils to be paired with the oscillation coils. At this time, since the switching unit (2) 1111 (FIG. 3) switches the connections between the amplification/filter unit and the plurality of the detection coils one by one, switching noise is generated. FIG. 5 shows a case where the noise is mixed with the first part after switching. The upper part of FIG. 5 shows detection waveforms 5100, and the lower part of FIG. 5 shows waveforms 5200 obtained after noise deletion processing. The waveforms 5200 after the noise deletion processing in the lower part of FIG. 5 is an instance where the waveform for the first one cycle is deleted and the waveforms of a time width T4 for the remaining 3 cycles are detected as signal components. The noise deletion processing can be operated by microcomputer (the time adjustment/detection unit 1160) loaded with CPU (Central Processing Unit).

Figure 6:
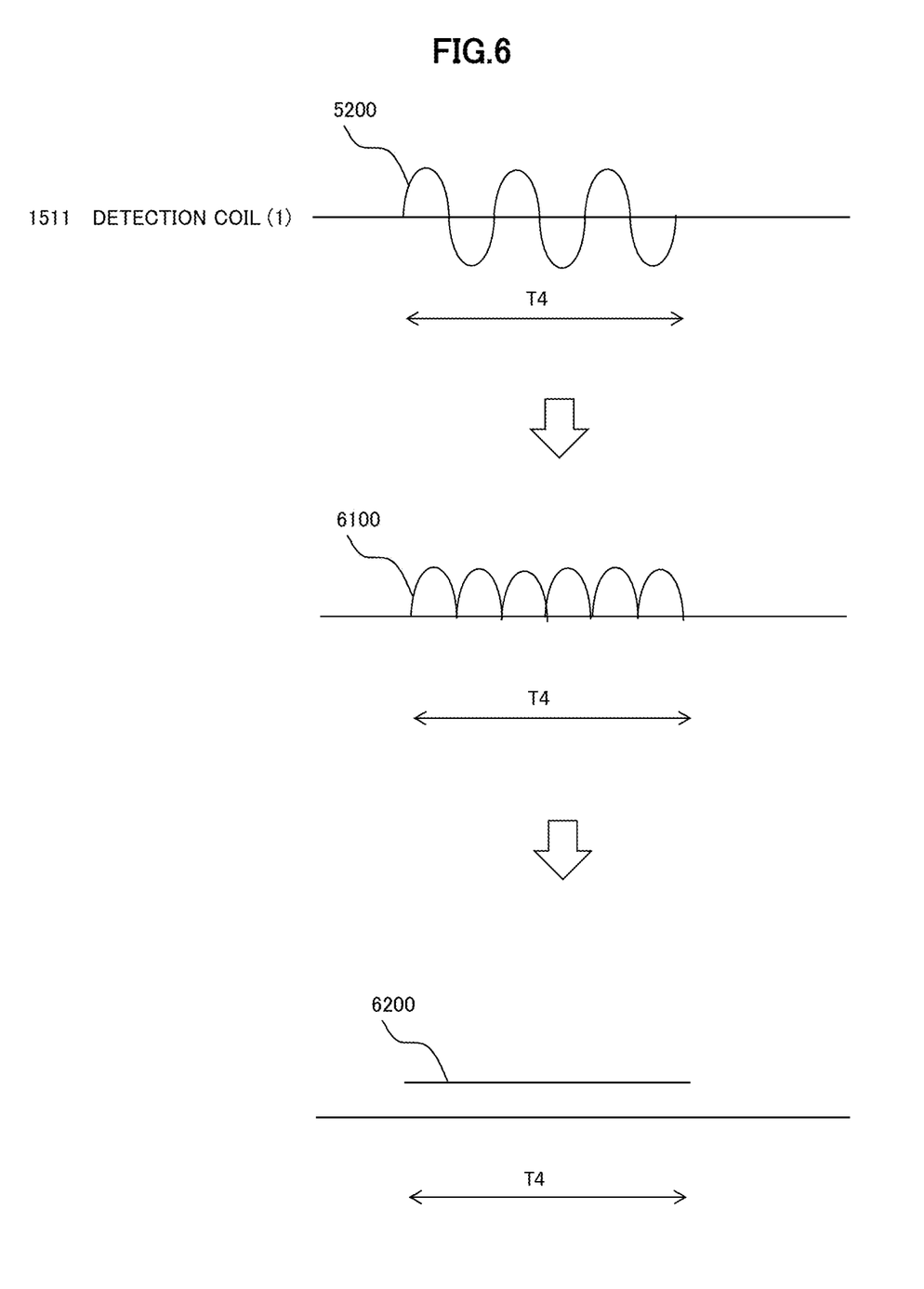
FIG. 6 is an exemplary diagram showing a method of the signal processing of the detection.

With reference to FIG. 6, a method of signal processing of the waveforms after the noise deletion processing will be described by taking the detection coil 1511 as an example. The waveforms 5200 after the noise deletion processing are subject to full-wave rectification for entirely converting negative signals to positive signals by the microcomputer (the time adjustment/detection unit 1160), so that waveforms 6100 after the detection are obtained. The waveforms 6100 after the detection are subject to time integration and divided by the number of data, so that waveforms 6200 averaged are obtained. Continuous movement waveforms are formed by setting the waveforms 6200 averaged to values at time 1, time 2, and time 3 (see FIG. 4).

The output signal 3200 shown in FIG. 3 indicates a voltage value corresponding to a relative distance between the oscillation coil (1) 1501 and the detection coil (2) 1511, for example, attached to the thumb and the index finger respectively, and a relative distance between the oscillation coil (2) 1502 and the detection coil (2) 1512 similarly attached to the thumb and the index finger respectively (a conversion formula between the relative distance and the voltage value will be described below).

(Assessment Apparatus) The assessment apparatus 1200 (see FIG. 1) records and analyzes the data measured by the movement function measurement apparatus 1100. Here, the assessment apparatus 1200 includes a data input unit 1210 for inputting the output signal (time sequential data) from the data communication unit 1600, a data processing unit 1220 for analyzing the output signal input, a signal control unit 1230 for transmitting a signal to start measurement to the movement function measurement apparatus 1100, a subject information processing unit 1240, an output-processing unit 1250 for converting the analysis result of the data processing unit 1220 into such a format as to be output on the display unit 1400, a storage unit 1260 for storing data processed by the data processing unit 1220 and the subject information processing unit 1240, a control unit 1270 for controlling data delivery and arithmetic processing or the like.

(Data Processing Unit) The data processing unit 1220 (see FIG. 1) calculates (forms) the movement waveforms of the finger tapping movements of the subject based on the output signal supplied from the data input unit 1210 and obtained through the control unit 1270 to calculate objective indexes to express severities of the movement function (for example, Parkinson's disease) and brain function (for example, dementia). Each of the information is stored in the storage unit 1260 appropriately.

Here, the data processing unit 1220 includes a Movement-waveform generating unit 1221 and a feature-amount generating unit 1222.

(Movement-Waveform Generating Unit) The movement-waveform generating unit 1221 (see FIG. 1) converts the time sequential data (waveform data) of the voltage output supplied from the movement function measurement apparatus 1100 into the corresponding movement waveforms, and performs time differentiation or time integration on the converted movement waveforms in order to complementarily generate a distance waveform, a velocity waveform, and an acceleration waveform (the detail will be described below).

Here, the conversion formula for converting the voltage output (voltage value) into the movement waveform (relative distance waveform or the like) is, for example, by using a calibration block formed by integrating a plurality of blocks indifferent lengths (for example, the blocks in lengths of 20, 30, 60 mm), calculated as an approximate curve in which a squared error of a dataset of voltage values and distance values obtained when the subject holds between the thumb and the index finger each section of the a plurality of lengths (20, 30, 60 mm) with the approximate curve becomes minimum.

Figure 7A:
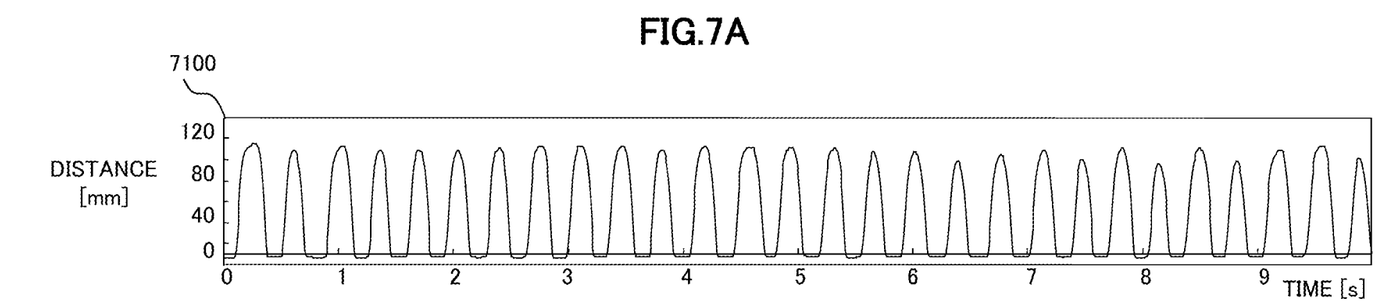
FIG. 7A is a diagram showing the distance waveform.
Figure 7B:
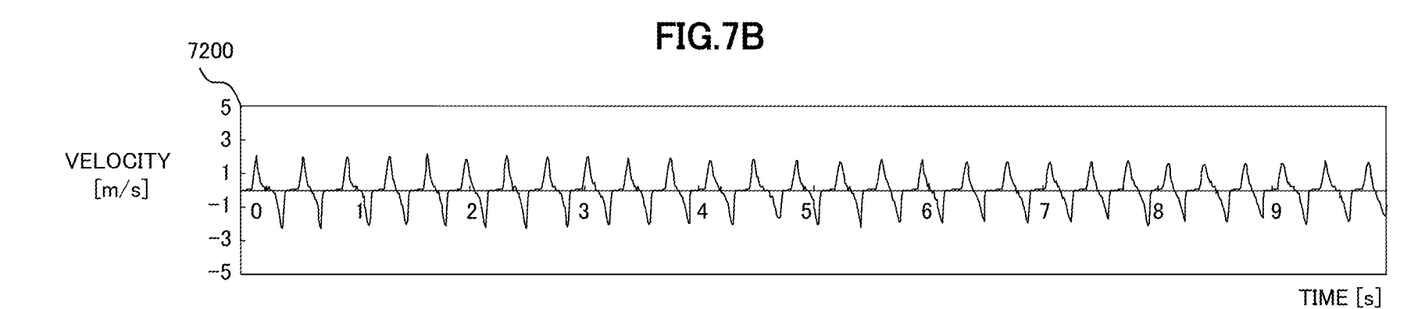
FIG. 7B is a diagram showing the velocity waveform.
Figure 7C:
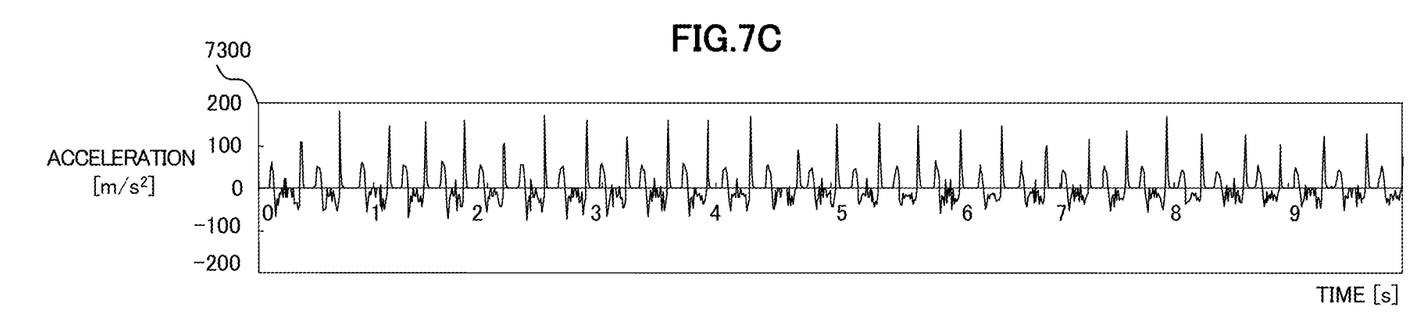
FIG. 7C is a diagram showing the acceleration waveform.

FIG. 7 shows a distance waveform 7100 (FIG. 7A) obtained by converting the waveform data by the conversion formula, a velocity waveform. 7200 (FIG. 7B) obtained by time differentiating the distance waveform 7100, and an acceleration waveform 7300 (FIG. 7C) obtained by time differentiating the velocity waveform 7200. Further, "movement waveform" includes, as long as not particularly limited, at least one of a distance waveform, a velocity waveform, an acceleration waveform, and a jerk waveform.

(Signal Control Unit) The signal control unit 1230 transmits the signal for starting the measurement to the movement function measurement unit 1100 in response to an operation signal supplied from the operating input unit 1300. The movement function measurement unit 1100 is a standby state while not performing the measurement, and becomes a state capable of measuring by the signal from the signal control unit 1230.

(Subject Information Processing Unit)

The subject information processing unit 1240 (see FIG. 1) includes a subject DB (Data Base) for recording the information such as the subject information and the analysis result in the storage unit 1260 to manage the information.

More specifically, the subject information processing unit 1240 performs generally four processes: (1) registers, corrects, deletes, searches, and sorts subject information; (2) associates subject information with measurement data; (3) registers, corrects, and deletes an analysis result of measurement data (adds, corrects, and deletes items); and (4) registers, corrects, and deletes a processed result of a statistical process when such statistical process was executed, together with the subject DB.

Examples of the subject information registered in the subject DB are a subject ID (Identifier), a name, birth date, age, height, weight, the name of disease, and a comment on the subject. Information management by the subject information processing unit 1240 can be easily realized by a conventionally well-known program and data structure.

(Output-Processing Unit) The output-processing unit 1250 (see FIG. 1) causes the display unit 1400 to display the subject information, information on an analysis result, etc., registered in the subject DB in a display form easily understandable visually which uses a graph, a table, etc, as needed. It is not necessary for the output processing unit 306 to cause the display unit 1400 to display all analysis results simultaneously, and the output processing unit 306 may be configured to cause the display unit 1400 to display only items selected accordingly by a user through the operating input unit 1300.

(Control Unit) The control unit 1270 (see FIG. 1) includes CPU (Central Processing Unit), ROM (Read Only Memory), and RAM (Random Access Memory) or the like.

Further, the movement-waveform generating unit 1221 and the feature-amount generating unit 1222 in the data processing unit 1220, the signal control unit 1230, the subject information processing unit 1240, and the output-processing unit 1250 are realized by loading the control unit 1270 with the programs or the data stored in the storage unit 1260 and executing the arithmetic processing.

(Operating Input Unit) The operating input unit 1300 (see FIG. 1) is for the user of the movement function assessment system 1000 to input the subject information, and is realized by, for example, a keyboard and a mouse. When the subject information is input, an input screen may be displayed on the display as a user interface that assists the input by the user.

(Display Unit) The display unit 1400 (see FIG. 1) displays the subject information and the movement information which were processed by the data processing unit 1220, and is realized by, for example, a LCD (Liquid Crystal Display) or a CRT (Cathode Ray Tube) display, and a printer.

Comparative Examples (Conventional Technologies)

Next, with reference to FIG. 8 and FIG. 9, and examples of output waveforms (FIG. 10 and FIG. 11) in each of the configurations, a technique used in the plurality of measurement points of the comparative examples (conventional technologies) will be described.

Figure 8:
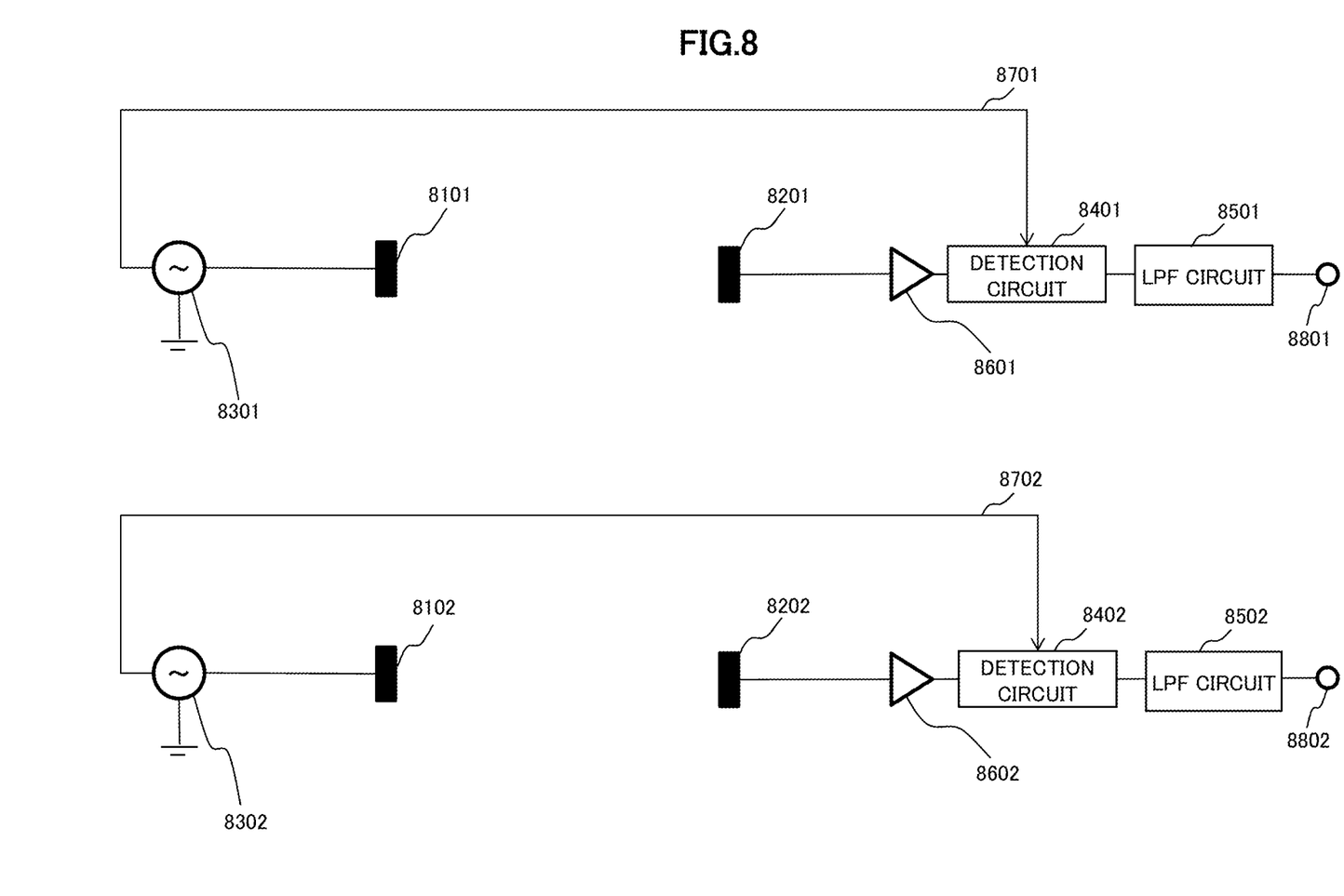
FIG. 8 is an exemplary diagram of a finger tapping measurement apparatus with 2 channels of the first comparative example (conventional technology).
Figure 10A:
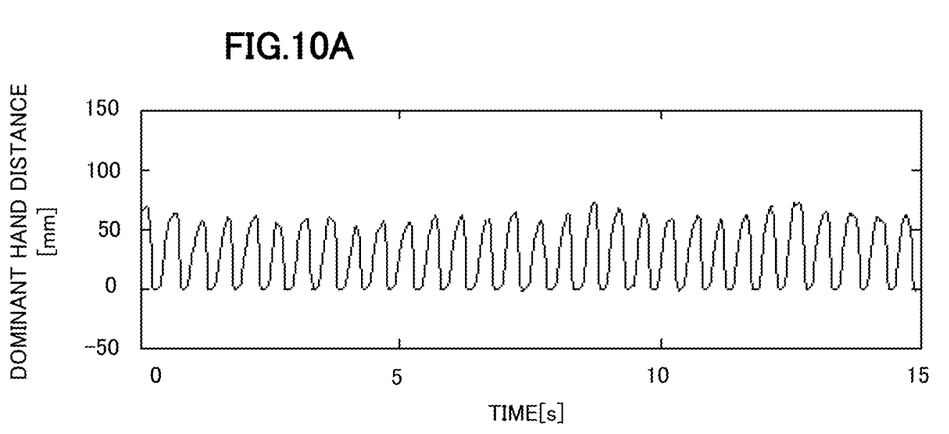
FIG. 10A is a diagram showing the distance waveform of the dominant hand.
Figure 10B:
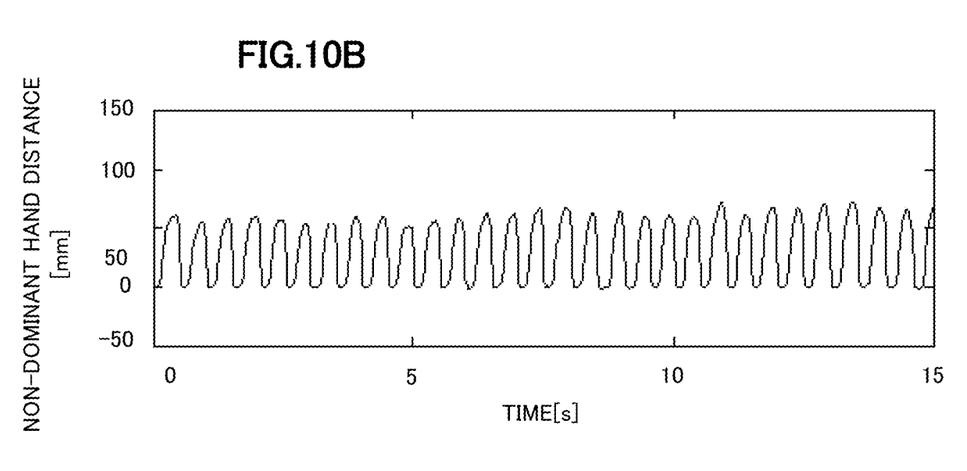
FIG. 10B is a diagram showing the distance waveform of the non-dominant hand.

In simultaneous measurement of the finger tapping movements of both hands of the first comparative example, as shown in FIG. 8, an alternating current generating circuit (f1) 8301 and an alternating current generating circuit (f2) 8302 generate the alternating currents having mutually different frequencies, and are connected with a oscillation coil (1) 8101 and a coil (2) 8202 respectively. Similarly, with respect to the detection coils, a detection coil (1) 8201 and a detection coil (2) 8202 are arranged respectively, and output signals 8801 and 8802 can be obtained respectively through amplification circuits 8601 and 8602, detection circuits 8401 and 8402, and low range pass filter circuits (LPF circuits) 8501 and 8502, and by using reference signals 8701 and 8702 respectively. FIG. 10 is the finger tapping movement waveforms of both hands simultaneously measured by a configuration of FIG. 8. FIG. 8A shows the distance waveform of a dominant hand, and FIG. 8B shows the distance waveform of a non-dominant hand. Further, with the configuration in this embodiment, waveforms which are exactly the same as the ones in FIG. 10 can be obtained.

Figure 9:
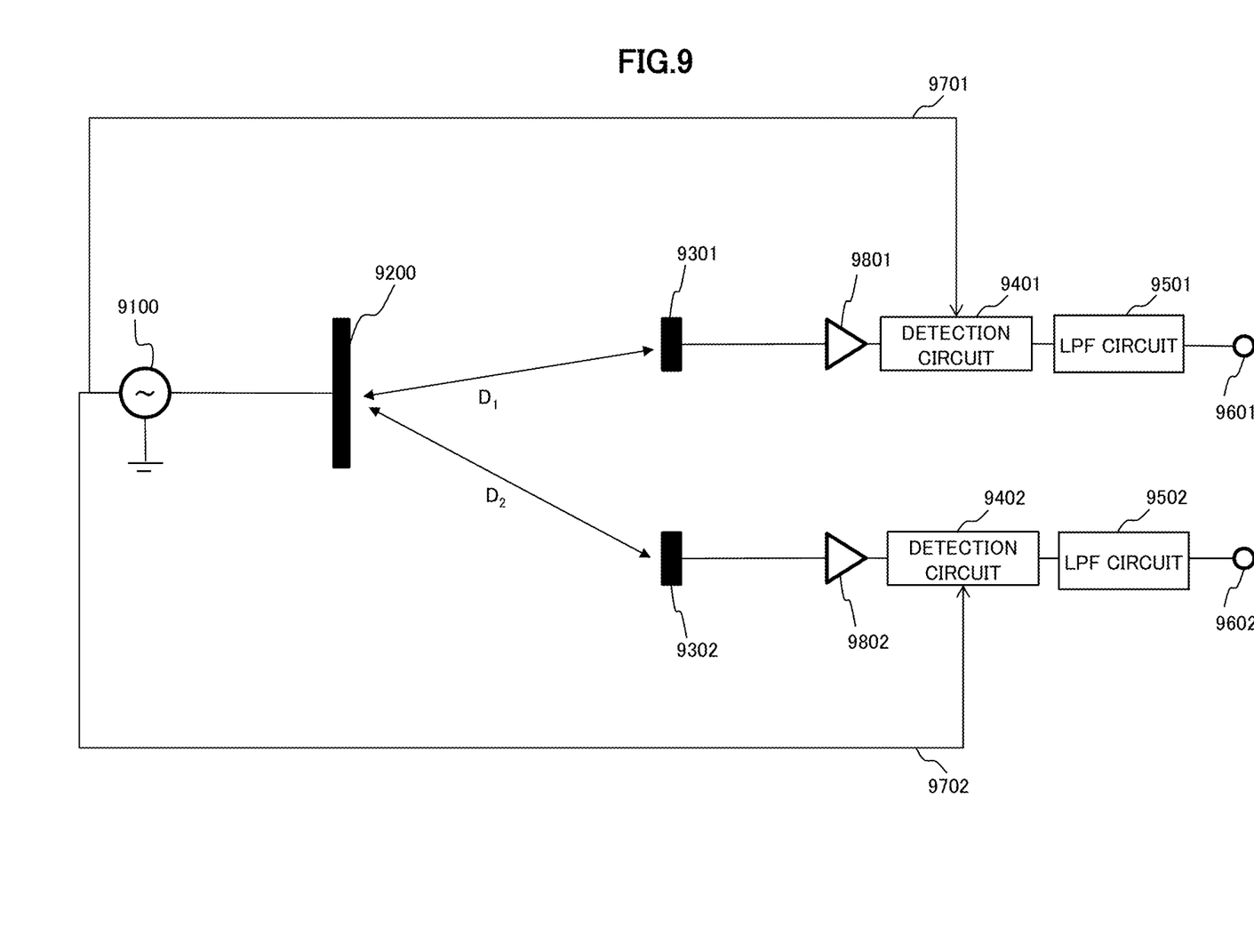
FIG. 9 is an exemplary diagram of a pulse measurement apparatus with 2 channels of the second comparative example (conventional technology).

In addition, another conventional example of a 2 channels simultaneous measurement of the second comparative example (conventional technology) is shown in FIG. 9. When distances D1 and D2 can be measured based on a oscillation coil 9200, one oscillation coil 9200 and one alternating current generating circuit 9100 are arranged, and two detection coils of a detection coil (1) 9301 and a detection coil (2) 9302 are arranged. Output signals 9601 and 9602 can be obtained respectively with respect to the detection coil (1) 9301 and the detection coil (2) 9302 through amplification circuits 9801 and 9802, detection circuits 9401 and 9402, and low-pass filter circuits (LPF circuits) 9501 and 9502, and by using reference signals 9701 and 9702 respectively.

Figure 11A:
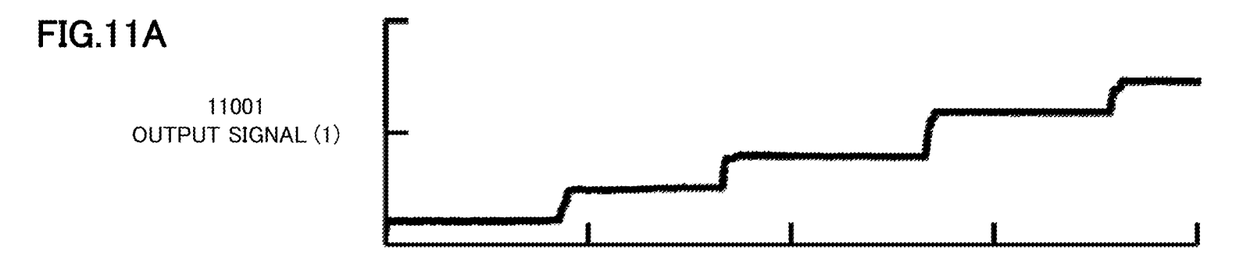
FIG. 11A is a diagram showing the stationary value corresponding to the blood pressure.
Figure 11B:
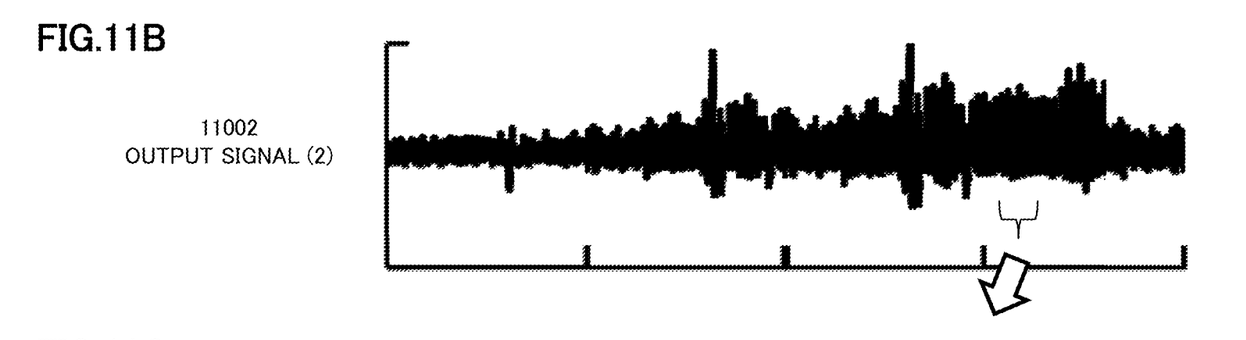
FIG. 11B and FIG. 11C are diagrams showing the brain wave.
Figure 11C:
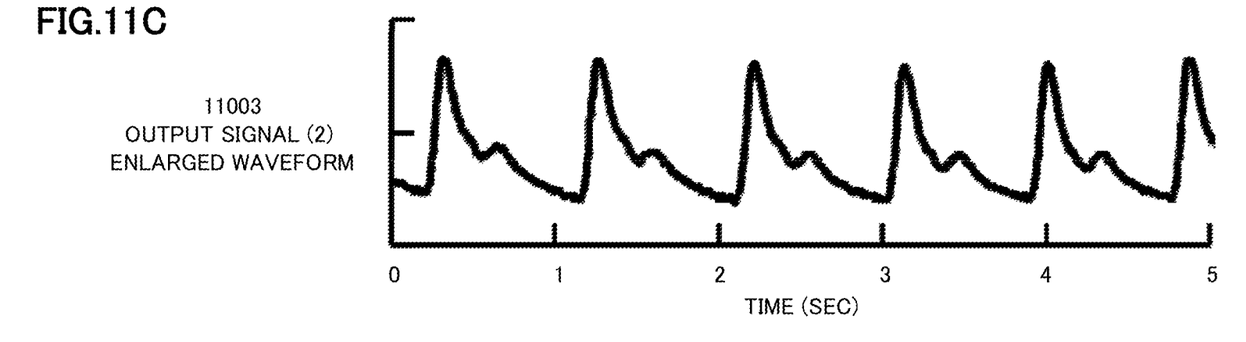

In the present configuration, a spring is arranged between D1 and D2 so as to maintain pressure on the biological object. Objects to be measured by such a configuration include brain waves such as carotid artery. FIG. 11 shows an example of the brain wave measured by the configuration of FIG. 9. As shown in FIG. 11A, an output signal (1) 11001 represents a stationary value corresponding to the blood pressure. As shown in FIG. 11B, output signal (2) 11002 represents the brain wave. Further, the output signal (1) 11001 at a position in which a local peak of amplitudes of the output signal (2) 11002 appears is a value corresponding to average blood pressure. Furthermore, as shown in FIG. 11C, a waveform obtained by enlarging the output signal (2) 11002 is an output signal (2) enlarged waveform 11003, in which the brain wave is clearly measured (observed).

Since in the comparative examples (conventional technologies) as shown in FIG. 8 to FIG. 11 as above, two circuit groups are arranged, it is possible to measure simultaneously at a plurality of sites of the biological object, however, it is not possible to realize miniaturization/power saving of circuit scale and reduction of communication capacity or the like.

(Effects) As explained above, according to the movement function assessment system 1000 of this embodiment, the movements of the biological object at a plurality of sites can be detected at approximately the same time (ignorable time lags at a plurality of points (T1*(N−1) at most in FIG. 4)). Further, a circuit scale is small so as to realize power saving and low cost. Furthermore, since the plurality of pairs consisting of the oscillation coils and the detection coils are switched to be used, it is possible to prevent the crosstalk (interference) between the two or more detection coils. In addition, since data amount to be handled can be reduced by down-sampling, it is possible to transmit easily the data to PC (Personal Computer) mainly by radio having limited communication capacity.

REFERENCE SIGNS LIST

1000 Movement function assessment system
1100 Movement function measurement apparatus
1110 Switching unit (1) (The first switching unit)
1111 Switching unit (2) (The second switching unit)
1120 Alternating current generating unit
1130 Amplification/filter unit
1140 Control unit
1150 Analog/digital conversion unit
1160 Time adjustment/detection unit
1170 Down-sampling unit
1200 Assessment unit
1210 Data input unit
1220 Data processing unit
1221 Movement-waveform generating unit
1222 Feature-amount generating unit
1230 Signal control unit
1240 Subject information processing unit
1250 Output-processing unit
1260 Storage unit
1270 Control unit
1300 Operating input unit
1400 Display unit
1500,1510 Sensor unit
1501, 1502, 150N Oscillation coil
1511, 1512, 151N Detection coil
1600 Data communication unit

What is claimed is:

1. A movement function measurement apparatus, comprising:

an alternating current generating unit configured to generate an alternating current of a predetermined frequency;

a plurality of oscillation coils;

a first switching unit connected with the alternating current generating unit, the first switching unit being configured to connect the alternating current generating unit with each of the plurality of oscillation coils one by one so that the alternating current of the predetermined frequency generated by the alternating current generating unit flows through each of the plurality of oscillation coils in sequence;

a plurality of detection coils, each of which is:
paired with a corresponding one of the plurality of oscillation coils; and
configured to output a detection signal, represented as a magnetic field waveform having a plurality of cycles over a period of time, based on a detection of a magnetic field generated by the corresponding one of the plurality of oscillation coils;

a second switching unit configured to connect with each of the plurality of detection coils one by one so that the detection signal from each of the plurality of detection coils is output to the second switching unit in sequence;

an amplification/filter unit connected with the plurality of detection coils through the second switching unit;

a detection unit connected with the amplification/filter unit, the detection unit being configured to perform detection by using reference signals from the alternating current generating unit; and a control unit configured to control the first switching unit and the second switching unit so that the magnetic field, generated by the corresponding one of the plurality of oscillation coils connected with the first switching unit, is detected by one of the plurality of detection coils which is paired with the corresponding one of the plurality of oscillation coils, connected with the second switching unit, wherein the movement function measurement apparatus is configured to calculate movement data including at least one of a distance data, velocity data, an acceleration data, and jerk data based on a relative distance between each of the coil pairs of the oscillation coils and the detection coils attached to movable portions of a biological object, the relative distance being obtained by converting a voltage value generated by each detection coil, and wherein, for each said magnetic field waveform obtained from a corresponding detection coil, the detection unit:
deletes a noise component contained in at least a first cycle in a period of time after the second switching unit is connected with the corresponding detection coil, and
detects remaining cycles in the period of time as a signal component.

2. The movement function measurement apparatus according to claim 1, wherein
the detection unit deletes, among the magnetic field waveforms obtained from each of the plurality of the detection coils, predetermined cycles thereof immediately after the second switching unit is connected with the each of the plurality of the detection coils.

3. The movement function measurement apparatus according to claim 2, wherein
the movement function measurement apparatus further includes a down-sampling unit configured to perform down-sampling of output data from the detection unit at a predetermined ratio.

4. The movement function measurement apparatus according to claim 2, wherein
the control unit controls the first switching unit and the second switching unit so that the alternating current flows through the each of the plurality of oscillation coils from the alternating current generating unit during a time width T1, and that the each of the coil pairs of the oscillation coils and the detection coils is functioned once for every cycle of a time width T2, in which
the control unit stops the alternating current generating unit during a time width T3 (T2−T1*N), wherein a number of the coil pairs of the oscillation coils and the detection coils is N, so that neither of the coil pairs of the oscillation coils and the detection coils is functioned.

5. The movement function measurement apparatus according to claim 2, further comprising:
an analog/digital conversion unit provided between the amplification/filter unit and the detection unit, the analog/digital conversion unit being configured to convert analog data received from the amplification/filter unit into digital data to transmit the digital data to the detection unit.

6. The movement function measurement apparatus according to claim 1, wherein
the movement function measurement apparatus further includes a down-sampling unit configured to perform down-sampling of output data from the detection unit at a predetermined ratio.

7. The movement function measurement apparatus according to claim 1, wherein
the control unit controls the first switching unit and the second switching unit so that the alternating current flows through the each of the plurality of oscillation coils from the alternating current generating unit during a time width T1, and that the each of the coil pairs of the oscillation coils and the detection coils is functioned once for every cycle of a time width T2, in which
the control unit stops the alternating current generating unit during a time width T3 (T2−T1*N), wherein a number of the coil pairs of the oscillation coils and the detection coils is N, so that neither of the coil pairs of the oscillation coils and the detection coils is functioned.

8. The movement function measurement apparatus according to claim 1, further comprising:
an analog/digital conversion unit provided between the amplification/filter unit and the detection unit, the analog/digital conversion unit being configured to convert analog data received from the amplification/filter unit into digital data to transmit the digital data to the detection unit.

9. A movement function assessment system, comprising:
the movement function measurement apparatus according to any one of claims 1-8; and
an assessment apparatus configured to assess a movement function of the biological object based on the movement data received from the movement function measurement apparatus.

10. The movement function assessment system according to claim 9, further comprising:
a data communication unit provided between the movement function measurement apparatus and the assessment apparatus, the data communication unit having a communication function to deliver by radio or cable the movement data on the plurality of the detection coils calculated by the movement function measurement apparatus all together to the assessment apparatus.

* * * * *